United States Patent [19]

Seele et al.

[11] Patent Number: 5,199,969
[45] Date of Patent: Apr. 6, 1993

[54] AZOLYLETHANE DERIVATIVES AND FUNGICIDES AND GROWTH REGULATORS CONTAINING THEM

[75] Inventors: Rainer Seele, Fussgoenheim; Walter Himmele, Walldorf; Reiner Kober, Fussgoenheim; Eberhard Ammermann, Ludwigshafen; Gisela Lorenz, Neustadt; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 660,724

[22] Filed: Feb. 25, 1991

Related U.S. Application Data

[63] Continuation of Ser. No. 503,923, Apr. 4, 1990, abandoned.

[30] Foreign Application Priority Data

May 6, 1989 [DE] Fed. Rep. of Germany ....... 3914944

[51] Int. Cl.$^5$ ................. A01N 43/653; C07D 249/08
[52] U.S. Cl. .................................. 504/272; 514/383;
548/268.2; 504/274; 504/275; 504/191;
504/169; 504/181; 504/185
[58] Field of Search ............................ 548/101, 268.2;
514/184, 383; 71/92

[56] References Cited

U.S. PATENT DOCUMENTS

| | | | |
|---|---|---|---|
| 4,315,016 | 2/1982 | Balassubramanyan et al. | 514/383 |
| 4,394,380 | 7/1983 | Balasubramanyan et al. | 514/383 |
| 4,507,140 | 3/1985 | Sugavanam | 71/76 |
| 4,549,027 | 10/1985 | Gates | 548/262 |

*Primary Examiner*—Patricia L. Morris
*Attorney, Agent, or Firm*—Oblon, Spivak, McClelland, Maier & Neustadt

[57] ABSTRACT

Azolylethane derivatives of the general formula I

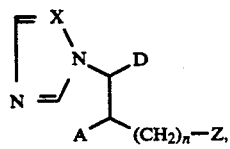

where A and Z are each alkyl, phenyl, biphenyl, naphthyl, benzyl, cycloalkyl or cycloalkenyl, these radicals being substituted or unsubstituted, D is alkoxy, amino, mercapto, thiophenyl, aminophenyl, hetaryloxy or phenoxy, these radicals being substituted or unsubstituted, n is an integer from 1 to 5 or 0, and X is CH or N, and their plant-tolerated acid addition salts and metal complexes, and fungicides and growth regulators containing these compounds.

16 Claims, No Drawings

AZOLYLETHANE DERIVATIVES AND FUNGICIDES AND GROWTH REGULATORS CONTAINING THEM

This is a continuation of application Ser. No. 07/503,923, filed on Apr. 4, 1990 now abandoned.

The present invention relates to novel azole compounds, processes for their preparation, and fungicides and growth regulators containing these compounds.

It is known that triazolylethane derivatives, e.g. 1-(1,2,4-triazol-1-yl)-1-phenylthio-2-methyl-2-phenylpropane or 1-(1,2,4-triazol-1-yl)-1-(4-chlorophenylthio)-2-methyl-2-phenylpropane, can be used as fungicides (European Patent 91,219). Their fungicidal action is unsatisfactory.

It is also known that triazolylalkoxybenzyl derivatives can be used as fungicides (DE-26 40 823).

We have found that azolylethane derivatives of the general formula I

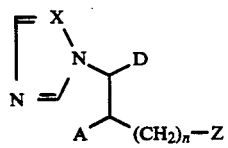

where
A and Z are each $C_1$–$C_8$-alkyl, phenyl, biphenyl, naphthyl, benzyl, tetrahydropyranyl, $C_3$–$C_8$-cycloalkyl or $C_5$–$C_8$-cycloalkenyl, where these radicals may be monosubstituted to trisubstituted by halogen, nitro, phenoxy, amino, alkyl, alkoxy or haloalkyl, each of 1 to 4 carbon atoms,
D is $C_1$–$C_4$-alkoxy, amino which is unsubstituted or substituted by $C_1$–$C_3$-alkyl or $C_1$–$C_3$-acyl, unsubstituted or $C_1$–$C_4$-alkyl-substituted mercapto, thiophenyl, aminophenyl, hetaryloxy or phenoxy, where these radicals may be monosubstituted to trisubstituted by halogen, nitro, phenoxy, amino, alkyl or haloalkyl, each of 1 to 4 carbon atoms,
n is an integer of from 1 to 5 or 0, and
X is CH or N,
and their plant-tolerated acid addition salts or metal complexes, except for the compounds in which A is unsubstituted phenyl, Z is alkyl, D is alkoxy, X is N and n is 0, have a better fungicidal action than the known azole compounds.

The compounds of the formula I contain asymmetric carbon atoms and can therefore occur as enantiomers and diastereomers. In the case of the novel compounds, the mixtures of diastereomers can be separated in a conventional manner, for example on the basis of their different solubilities or by column chromatography, and can be isolated in pure form The racemates of the novel compounds can be resolved by known methods, for example by salt formation with an optically active acid, separation of the diastereomeric salts and liberation of the enantiomers by means of a base Both the individual enantiomers or diastereomers and mixtures thereof can be used as fungicidal and growth-regulating active ingredients.

A and Z are identical or different and are each, for example, $C_1$–$C_4$-alkyl, methyl, ethyl, isopropyl, n-propyl, n-butyl, sec-butyl, tert-butyl, n-pentyl, neopentyl, 1-naphthyl, 2-naphthyl, p-biphenyl, phenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, 2-methoxyphenyl, 3-methoxyphenyl, 4-methoxyphenyl, 2,4-dimethoxyphenyl, 4-ethylphenyl, 4-isopropylphenyl, 4-tert-butylphenyl, 4-tertbutoxyphenyl, 2-chloro-4-fluorophenyl,2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-aminophenyl, 2-trifluoromethylphenyl, 3-trifluoromethylphenyl, 4-trifluoromethylphenyl, tetrahydropyranyl, cyclopropyl, cyclopentyl, cyclohexyl, 2-cyclohexenyl or 3-cyclohexenyl.

n is 0, 1, 2, 3, 4 or 5.

Acid addition salts are, for example, the hydrochlorides, bromides, sulfates, nitrates, phosphates, oxalates or dodecylbenzenesulfonates. The activity of the salts is due to the cation, so that the anion is in general unimportant. The novel active ingredient salts are prepared by reacting the azolylethane derivatives (I) with the acids.

Metal complexes of the active ingredients I or their salts can be formed with copper, zinc, tin, manganese, iron, cobalt or nickel by reacting the azolylethane derivatives with corresponding metal salts Compounds of the formula I can be prepared by reacting a compound of the formula II

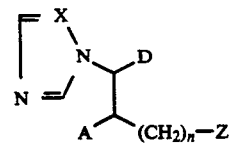

where A, Z and X have the abovementioned meanings and Hal is chlorine or bromine, with a compound of the formula D–H.

The reaction is carried out in the presence or absence of a solvent or diluent, with or without the addition of an inorganic or organic base and of a reaction accelerator, at from 10° to 150° C. The preferred solvents and diluents include ketones, such as acetone, methyl ethyl ketone or cyclohexanone, nitriles, such as acetonitrile or propionitrile, alcohols, such as methanol, ethanol, isopropanol, n-butanol or glycol, esters, such as ethyl acetate, methyl acetate or butyl acetate, ethers, such as tetrahydrofuran, diethyl ether, dimethoxyethane, dioxane or diisopropyl ether, amides, such as dimethylformamide or N-methylpyrrolidone, as well as dimethyl sulfoxide, sulfolane or mixtures thereof.

Suitable bases which may also be used as acid acceptors in the reaction are, for example, alkali metal hydroxides, such as lithium hydroxide, sodium hydroxide or potassium hydroxide, alkali metal carbonates, such as sodium carbonate, potassium carbonate or cesium carbonate, alkali metal hydrides, such as lithium hydride, sodium hydride and potassium hydride, alkali metal amides, such as sodium amide and potassium amide, as well as triphenylmethyllithium, triphenylmethylsodium, triphenylmethylpotassium, naphthalenelithium, naphthalenesodium, naphthalenepotassium, pyridine or 4-dimethylaminopyridine. However, other conventional bases may also be used.

Preferred reaction accelerators are metal halides, such as sodium iodide or potassium iodide, quaternary ammonium salts, such as tetrabutylammonium chloride, bromide, iodide or hydrogen sulfate or benzyltriethylammonium chloride or bromide, or crown ethers, such as 12-crown-4, 15-crown-5, 18-crown-6, dibenzo-18-crown-6 or dicyclohexano-18-crown-6.

The reaction is carried out in general at from 20° to 150° C. under atmospheric or superatmospheric pressure, continuously or batchwise.

The starting compounds II can be prepared by reacting a compound of the formula III

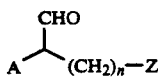

where A, Z and n have the abovementioned meanings, with a compound of the formula IV

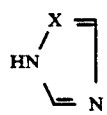

where X has the abovementioned meanings, in the presence of a thionyl halide.

The reaction is carried out in the presence or absence of a solvent or diluent at from −30° to 80° C. The preferred solvents or diluents include nitriles, such as acetonitrile or propionitrile, ethers, such as tetrahydrofuran, diethyl ether, dimethoxyethane, dioxane or diisopropyl ether, and in particular hydrocarbons and chlorohydrocarbons, such as pentane, hexane, methylene chloride, chloroform, carbon tetrachloride, dichloroethane or mixtures thereof.

The compounds III can be prepared by generally methods of aldehyde synthesis (Houben-Weyl-Müller, 1983, Vol. E).

The Examples which follow illustrate the preparation of the active ingredients.

1. Preparation of the starting materials
Method 1
1-(1,2,4-Triazol-1-yl)-1-chloro-2-(2,4-dichlorophenyl)-butane 132.8 g of thionyl chloride are added to a solution of 307.9 g of triazole in 500 ml of methylene chloride at 0° C. After the end of the addition, the mixture is stirred at room temperature (20° C.) for 30 minutes and 116.3 g of 2-(2,4-dichlorophenyl)-butanal are then added. The reaction mixture is stirred for 15 hours at room temperature, after which 400 ml of water are added to the solution and the organic phase is separated off. The remaining aqueous phase is extracted twice by shaking with methylene chloride and the collected organic phases are washed twice with saturated sodium bicarbonate solution. The organic phase isolated is then dried over sodium sulfate and evaporated down, 158.2 g of 1-(1,2,4-triazol-1-yl)-1-chloro-2-(2,4-dichlorophenyl)-butane being obtained.

2. Preparation of the end products

EXAMPLE 1

1-(1,2,4-Triazol-1-yl)-1-methoxy-2-(2,4-dichlorophenyl)butane 9.4 g of sodium methylate and 0.2 g of potassium iodide are added to a solution of 26.6 g of 1-(1,2,4-triazol-1-yl)-1-chloro-2-(2,4-dichlorophenyl)-butane in 200 ml of methanol. The reaction mixture is refluxed for 48 hours, after which 100 ml of water are added to the solution and the mixture is extracted several times with methyl tert-butyl ether. The organic phase isolated is washed twice with water, then dried over sodium sulfate and evaporated down and the remaining residue is purified by chromatography over silica gel (9:1 ethyl acetate/n-hexane). 6.2 g (24%) of 1-(1,2,4-triazol-1-yl)-1-methoxy-2-(2,4-dichlorophenyl)-butane are obtained as a 1:1 diastereomer mixture [compound No. 1).

The compounds listed in the Table can be prepared similarly to Example 1.

TABLE

Fungicidal azolylethane derivatives

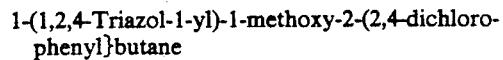

I

| Ex. | A | Z | D | n | X | m.p./IR (cm$^{-1}$) | Isomer* |
|---|---|---|---|---|---|---|---|
| 1 | 2,4-Cl$_2$—C$_6$H$_3$ | CH$_3$ | OCH$_3$ | 1 | N | 2968, 1502, 1475, 1275 1135, 1103, 806 cm$^{-1}$ | D$_1$:D$_2$ = 1:1 |
| 2 | 2,4-Cl$_2$—C$_6$H$_3$ | CH$_3$ | OCH$_3$ | 1 | CH | | |
| 3 | 2,4-Cl$_2$—C$_6$H$_3$ | CH$_3$ | OC$_2$H$_5$ | 1 | N | | |
| 4 | 2,4-Cl$_2$—C$_6$H$_3$ | CH$_3$ | 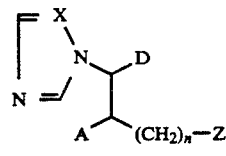 | 1 | N | | |
| 5 | 2,4-Cl$_2$—C$_6$H$_3$ | CH$_3$ | S—CH$_3$ | 1 | N | | |
| 6 | 2,4-Cl$_2$—C$_6$H$_3$ | CH$_3$ | S—CH$_3$ | 1 | CH | | |
| 7 | 2,4-Cl$_2$—C$_6$H$_3$ | CH$_3$ | NHCH$_3$ | 1 | N | | |
| 8 | 2,4-Cl$_2$—C$_6$H$_3$ | CH$_3$ | N(CH$_3$)$_2$ | 1 | N | | |
| 9 | 2,4-Cl$_2$—C$_6$H$_3$ | CH$_3$ | NH$_2$ | 1 | N | | |
| 10 | 2,4-Cl$_2$—C$_6$H$_3$ | CH$_3$ | S—C$_6$H$_5$ | 1 | N | | |
| 11 | 2,4-Cl$_2$—C$_6$H$_3$ | CH$_3$ | NH—C$_6$H$_5$ | 1 | N | | |
| 12 | 2,4-Cl$_2$—C$_6$H$_3$ | CH$_3$ | O—C$_6$H$_5$ | 1 | N | | |

TABLE-continued

Fungicidal azolylethane derivatives

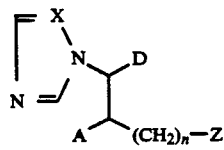

I

| Ex. | A | Z | D | n | X | m.p./IR (cm$^{-1}$) | Isomer* |
|---|---|---|---|---|---|---|---|
| 13 | 2,4-Cl$_2$—C$_6$H$_3$ | CH$_3$ | ⟨4-Cl-C$_6$H$_4$-O—⟩ | 1 | N | | |
| 14 | 2,4-Cl$_2$—C$_6$H$_3$ | CH$_3$ | ⟨2,4-Cl$_2$-C$_6$H$_3$-O—⟩ | 1 | N | | |
| 15 | 2,4-Cl$_2$—C$_6$H$_3$ | CH$_3$ | ⟨4-F-C$_6$H$_4$-O—⟩ | 1 | N | | |
| 16 | 2,4-Cl$_2$—C$_6$H$_3$ | CH$_3$ | OCH$_3$ | 0 | N | | |
| 17 | 2,4-Cl$_2$—C$_6$H$_3$ | CH$_3$ | OCH$_3$ | 0 | CH | | |
| 18 | 2,4-Cl$_2$—C$_6$H$_3$ | CH$_3$ | OC$_2$H$_5$ | 0 | N | | |
| 19 | 2,4-Cl$_2$—C$_6$H$_3$ | CH$_3$ | OC$_2$H$_5$ | 0 | CH | | |
| 20 | 2,4-Cl$_2$—C$_6$H$_3$ | CH$_3$ | S—CH$_3$ | 0 | N | | |
| 21 | 2,4-Cl$_2$—C$_6$H$_3$ | CH$_3$ | NH—COCH$_3$ | 1 | N | | |
| 22 | 2,4-Cl$_2$—C$_6$H$_3$ | CH$_3$ | NH$_2$ | 0 | N | | |
| 23 | 2,4-Cl$_2$—C$_6$H$_3$ | CH$_3$ | ⟨4-Cl-C$_6$H$_4$-O—⟩ | 0 | N | | |
| 24 | 2,4-Cl$_2$—C$_6$H$_3$ | CH$_3$ | O—C$_6$H$_5$ | 0 | N | | |
| 25 | 2,4-Cl$_2$—C$_6$H$_3$ | CH$_3$ | ⟨2,4-Cl$_2$-C$_6$H$_3$-O—⟩ | 0 | N | | |
| 26 | 2,4-Cl$_2$—C$_6$H$_3$ | CH$_3$ | ⟨2,4-Cl$_2$-C$_6$H$_3$-O—⟩ | 0 | CH | | |
| 27 | 2,4-Cl$_2$—C$_6$H$_3$ | CH$_3$ | OCH$_3$ | 2 | N | 1960, 1502, 1475, 1275 1134, 1103, 823 cm$^{-1}$ | D$_1$:D$_2$ = 1:1 |
| 28 | 2,4-Cl$_2$—C$_6$H$_3$ | CH$_3$ | OCH$_3$ | 2 | CH | | |
| 29 | 2,4-Cl$_2$—C$_6$H$_3$ | CH$_3$ | OC$_2$H$_5$ | 2 | N | | |
| 30 | 2,4-Cl$_2$—C$_6$H$_3$ | CH$_3$ | OC$_2$H$_5$ | 2 | CH | | |
| 31 | 2,4-Cl$_2$—C$_6$H$_3$ | CH$_3$ | O—CH(CH$_3$)$_2$ | 2 | N | | |
| 32 | 2,4-Cl$_2$—C$_6$H$_3$ | CH$_3$ | SCH$_3$ | 2 | N | | |
| 33 | 2,4-Cl$_2$—C$_6$H$_3$ | CH$_3$ | S—C$_3$H$_7$ | 2 | N | | |
| 34 | 2,4-Cl$_2$—C$_6$H$_3$ | CH$_3$ | NH$_2$ | 2 | N | | |
| 35 | 2,4-Cl$_2$—C$_6$H$_3$ | CH$_3$ | S—C$_6$H$_5$ | 2 | N | 75–78° C. | enantiomer mixture |
| 36 | 2,4-Cl$_2$—C$_6$H$_3$ | CH$_3$ | NH—C$_6$H$_5$ | 2 | N | | |
| 37 | 2,4-Cl$_2$—C$_6$H$_3$ | CH$_3$ | O—C$_6$H$_5$ | 2 | N | | |

TABLE-continued

Fungicidal azolylethane derivatives

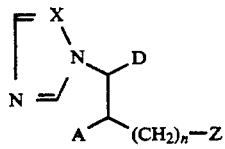

I

| Ex. | A | Z | D | n | X | m.p./IR (cm$^{-1}$) | Isomer* |
|---|---|---|---|---|---|---|---|
| 38 | 2,4-Cl$_2$—C$_6$H$_3$ | CH$_3$ | 4-Cl-C$_6$H$_4$-O— | 2 | N | | |
| 39 | 2,4-Cl$_2$—C$_6$H$_3$ | CH$_3$ | 2,4-Cl$_2$-C$_6$H$_3$-O— | 2 | N | | |
| 40 | 2,4-Cl$_2$—C$_6$H$_3$ | CH$_3$ | 2,4-Cl$_2$-C$_6$H$_3$-O— | 2 | CH | | |
| 41 | 2,4-Cl$_2$—C$_6$H$_3$ | CH$_3$ | 4-F-C$_6$H$_4$-O— | 2 | N | | |
| 42 | 2,4-Cl$_2$—C$_6$H$_3$ | CH$_3$ | OCH$_3$ | 3 | N | 2957, 1501, 1475, 1275 1104, 809 cm$^{-1}$ | D$_1$:D$_2$ = 1,2:1 |
| 43 | 2,4-Cl$_2$—C$_6$H$_3$ | CH$_3$ | OCH$_3$ | 3 | CH | | |
| 44 | 2,4-Cl$_2$—C$_6$H$_3$ | CH$_3$ | OC$_2$H$_5$ | 3 | N | 2957, 1500, 1474, 1274 1132, 1103, 807 cm$^{-1}$ | D$_1$:D$_2$ = 1:1 |
| 45 | 2,4-Cl$_2$—C$_6$H$_3$ | CH$_3$ | OC$_4$H$_9$ | 3 | N | | |
| 46 | 2,4-Cl$_2$—C$_6$H$_3$ | CH$_3$ | SCH$_3$ | 3 | N | | |
| 47 | 2,4-Cl$_2$—C$_6$H$_3$ | CH$_3$ | N(CH$_3$)$_2$ | 3 | N | | |
| 48 | 2,4-Cl$_2$—C$_6$H$_3$ | CH$_3$ | O—C$_6$H$_5$ | 3 | N | | |
| 49 | 2,4-Cl$_2$—C$_6$H$_3$ | CH$_3$ | 4-Cl-C$_6$H$_4$-O— | 3 | N | 2957, 1504, 1490, 1475, 1275, 1135, 825, 805 cm$^{-1}$ | D$_1$:D$_2$ = 1:1 |
| 50 | 2,4-Cl$_2$—C$_6$H$_3$ | CH$_3$ | 2,4-Cl$_2$-C$_6$H$_3$-O— | 3 | N | | |
| 51 | 2,4-Cl$_2$—C$_6$H$_3$ | CH$_3$ | S—C$_6$H$_5$ | 3 | N | | |
| 52 | 2,4-Cl$_2$—C$_6$H$_3$ | CH$_3$ | OCH$_3$ | 4 | N | | |
| 53 | 2,4-Cl$_2$—C$_6$H$_3$ | CH$_3$ | OCH$_3$ | 4 | CH | | |
| 54 | 2,4-Cl$_2$—C$_6$H$_3$ | CH$_3$ | OCH$_3$ | 5 | N | | |
| 55 | 2,4-Cl$_2$—C$_6$H$_3$ | CH$_3$ | OCH$_3$ | 5 | CH | | |
| 56 | C$_6$H$_5$ | CH$_3$ | OCH$_3$ | 0 | N | | |
| 57 | C$_6$H$_5$ | CH$_3$ | OCH$_3$ | 0 | CH | | |
| 58 | C$_6$H$_5$ | CH$_3$ | NH$_2$ | 0 | N | | |
| 59 | C$_6$H$_5$ | CH$_3$ | SCH$_3$ | 0 | N | | |
| 60 | C$_6$H$_5$ | CH$_3$ | OC$_6$H$_5$ | 0 | N | | |
| 61 | C$_6$H$_5$ | CH$_3$ | SC$_6$H$_5$ | 0 | N | | |
| 62 | C$_6$H$_5$ | CH$_3$ | 4-Cl-C$_6$H$_4$-O— | 0 | N | | |

TABLE-continued

Fungicidal azolylethane derivatives

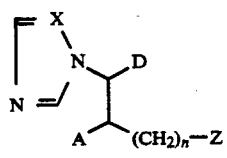

I

| Ex. | A | Z | D | n | X | m.p./IR (cm$^{-1}$) | Isomer* |
|---|---|---|---|---|---|---|---|
| 63 | $C_6H_5$ | $CH_3$ | 2,4-Cl$_2$-C$_6$H$_3$-O- | 0 | N | | |
| 64 | $C_6H_5$ | $CH_3$ | $OCH_3$ | 1 | N | 1501, 1274, 1135, 701; | $D_1:D_2 = 1:1$ |
| 65 | $C_6H_5$ | $CH_3$ | $OC_2H_5$ | 1 | N | | |
| 66 | $C_6H_5$ | $CH_3$ | $SCH_3$ | 1 | N | | |
| 67 | $C_6H_5$ | $CH_3$ | 4-Cl-C$_6$H$_4$-O- | 1 | N | | |
| 68 | $C_6H_5$ | $CH_3$ | $OCH_3$ | 2 | N | | |
| 69 | $C_6H_5$ | $CH_3$ | $OC_2H_5$ | 2 | N | | |
| 70 | $C_6H_5$ | $CH_3$ | $O$-iPr | 2 | N | | |
| 71 | $C_6H_5$ | $CH_3$ | $SCH_3$ | 2 | N | | |
| 72 | $C_6H_5$ | $CH_3$ | $NH-C_6H_5$ | 2 | N | | |
| 73 | $C_6H_5$ | $CH_3$ | 4-Cl-C$_6$H$_4$-O- | 2 | N | | |
| 74 | $C_6H_5$ | $CH_3$ | $OCH_3$ | 3 | N | 2955, 2932, 1498, 1274, 1135, 1102, 701 cm$^{-1}$ | $D_1:D_2 = 1:1$ |
| 75 | $C_6H_5$ | $CH_3$ | $OC_2H_5$ | 3 | N | | |
| 76 | $C_6H_5$ | $CH_3$ | $SCH_3$ | 3 | N | | |
| 77 | $C_6H_5$ | $CH_3$ | 4-Cl-C$_6$H$_4$-O- | 3 | N | | |
| 78 | $C_6H_5$ | $CH_3$ | $OCH_3$ | 4 | N | | |
| 79 | $C_6H_5$ | $CH_3$ | $OCH_3$ | 5 | N | 2928, 1499, 1274, 1135, 701 | $D_1:D_2 = 1:1$ |
| 80 | $C_6H_5$ | $C_6H_5$ | $OCH_3$ | 1 | N | | |
| 81 | $C_6H_5$ | $C_6H_5$ | $OC_2H_5$ | 1 | N | | |
| 82 | $C_6H_5$ | $C_6H_5$ | $SCH_3$ | 1 | N | | |
| 83 | $C_6H_5$ | $C_6H_5$ | 4-Cl-C$_6$H$_4$-O- | 1 | N | | |
| 84 | $C_6H_5$ | $C_{10}H_7$ | $OCH_3$ | 1 | N | | |
| 85 | $C_6H_5$ | $C_{12}H_9$ | $OCH_3$ | 1 | N | | |
| 86 | $C_6H_5$ | 2,4-Cl$_2$-C$_6$H$_3$ | $OCH_3$ | 1 | N | | |
| 87 | $C_6H_5$ | 2,4-Cl$_2$-C$_6$H$_3$ | $OCH_3$ | 2 | N | | |
| 88 | $C_6H_5$ | 4-F-C$_6$H$_4$ | $OCH_3$ | 1 | N | | |
| 89 | $C_6H_5$ | 2-Cl-C$_6$H$_4$ | $OCH_3$ | 1 | N | | |
| 90 | $C_6H_5$ | 4-Cl-C$_6$H$_4$ | $OCH_3$ | 1 | N | | |
| 91 | $C_6H_5$ | cyclohexyl | $OCH_3$ | 1 | N | | |
| 92 | $C_6H_5$ | cyclohexyl | $OCH_3$ | 1 | CH | | |
| 93 | $C_6H_5$ | cyclohexyl | $OCH_3$ | 0 | N | | |
| 94 | $C_6H_5$ | cyclohexyl | $SCH_3$ | 0 | N | | |

TABLE-continued

Fungicidal azolylethane derivatives

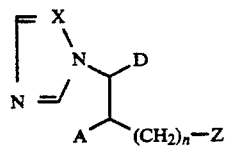

I

| Ex. | A | Z | D | n | X | m.p./IR (cm$^{-1}$) | Isomer* |
|---|---|---|---|---|---|---|---|
| 95 | C$_6$H$_5$ | cyclohexyl | O-C$_6$H$_4$-Cl (4-Cl) | 0 | N | | |
| 96 | 4-F—C$_6$H$_4$ | iso-C$_3$H$_7$ | OCH$_3$ | 0 | N | | |
| 97 | 4-F—C$_6$H$_4$ | iso-C$_3$H$_7$ | OC$_2$H$_5$ | 0 | N | | |
| 98 | 4-F—C$_6$H$_4$ | iso-C$_3$H$_7$ | SCH$_3$ | 0 | N | | |
| 99 | 4-F—C$_6$H$_4$ | iso-C$_3$H$_7$ | OC$_6$H$_5$ | 0 | N | | |
| 100 | 4-F—C$_6$H$_4$ | iso-C$_3$H$_7$ | O-C$_6$H$_4$-Cl (4-Cl) | 0 | N | | |
| 101 | 4-F—C$_6$H$_4$ | cyclohexyl | OCH$_3$ | 0 | N | | |
| 102 | 4-F—C$_6$H$_4$ | 3-cyclohexyl | OCH$_3$ | 0 | N | | |
| 103 | 4-F—C$_6$H$_4$ | CH$_3$ | OCH$_3$ | 0 | N | | |
| 104 | 4-F—C$_6$H$_4$ | CH$_3$ | OC$_2$H$_5$ | 0 | N | | |
| 105 | 4-F—C$_6$H$_4$ | CH$_3$ | SCH$_3$ | 0 | N | | |
| 106 | 4-F—C$_6$H$_4$ | CH$_3$ | O-C$_6$H$_4$-Cl (4-Cl) | 0 | N | | |
| 107 | 4-F—C$_6$H$_4$ | CH$_3$ | OCH$_3$ | 1 | N | | |
| 108 | 4-F—C$_6$H$_4$ | CH$_3$ | SCH$_3$ | 1 | N | | |
| 109 | 4-F—C$_6$H$_4$ | CH$_3$ | OC$_6$H$_5$ | 1 | N | | |
| 110 | 4-F—C$_6$H$_4$ | CH$_3$ | SC$_6$H$_5$ | 1 | N | | |
| 111 | 4-F—C$_6$H$_4$ | CH$_3$ | O-C$_6$H$_4$-Cl (4-Cl) | 1 | N | | |
| 112 | 4-F—C$_6$H$_4$ | CH$_3$ | OCH$_3$ | 2 | N | | |
| 113 | 4-F—C$_6$H$_4$ | CH$_3$ | SCH$_3$ | 2 | N | | |
| 114 | 4-F—C$_6$H$_4$ | CH$_3$ | HNC$_6$H$_5$ | 2 | N | | |
| 115 | 4-F—C$_6$H$_4$ | CH$_3$ | OCH$_3$ | 3 | N | | |
| 116 | 4-F—C$_6$H$_4$ | CH$_3$ | SCH$_3$ | 3 | N | | |
| 117 | 4-F—C$_6$H$_4$ | CH$_3$ | OCH$_3$ | 5 | N | | |
| 118 | 4-F—C$_6$H$_4$ | C$_6$H$_5$ | OCH$_3$ | 1 | N | | |
| 119 | 4-F—C$_6$H$_4$ | 4-Cl—C$_6$H$_4$ | OCH$_3$ | 1 | N | | |
| 120 | 4-F—C$_6$H$_4$ | 4-F—C$_6$H$_4$ | OCH$_3$ | 1 | N | | |
| 121 | 4-F—C$_6$H$_4$ | 4-OCH$_3$—C$_6$H$_4$ | OCH$_3$ | 1 | N | | |
| 122 | 4-F—C$_6$H$_4$ | 2-Cl—C$_6$H$_4$ | OCH$_3$ | 1 | N | | |
| 123 | 4-Cl—C$_6$H$_4$ | iso-C$_3$H$_7$ | OCH$_3$ | 1 | N | | |
| 124 | 4-Cl—C$_6$H$_4$ | iso-C$_3$H$_7$ | SCH$_3$ | 1 | N | | |
| 125 | 4-Cl—C$_6$H$_4$ | iso-C$_3$H$_7$ | O-C$_6$H$_4$-Cl (4-Cl) | 1 | N | | |
| 126 | 4-Cl—C$_6$H$_4$ | cyclohexyl | OCH$_3$ | 0 | N | | |
| 127 | 4-Cl—C$_6$H$_4$ | 2-cyclohexenyl | OCH$_3$ | 0 | N | | |
| 128 | 4-Cl—C$_6$H$_4$ | CH$_3$ | OCH$_3$ | 0 | N | | |
| 129 | 4-Cl—C$_6$H$_4$ | CH$_3$ | OC$_2$H$_5$ | 0 | N | | |
| 130 | 4-Cl—C$_6$H$_4$ | CH$_3$ | SCH$_3$ | 0 | N | | |

TABLE-continued

Fungicidal azolylethane derivatives

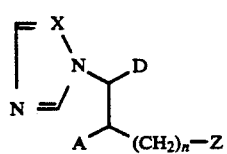

I

| Ex. | A | Z | D | n | X | m.p./IR (cm$^{-1}$) | Isomer* |
|---|---|---|---|---|---|---|---|
| 131 | 4-Cl—C$_6$H$_4$ | CH$_3$ | O—C$_6$H$_4$—Cl (4-Cl-phenoxy) | 0 | N | | |
| 132 | 4-Cl—C$_6$H$_4$ | CH$_3$ | OCH$_3$ | 1 | N | | |
| 133 | 4-Cl—C$_6$H$_4$ | CH$_3$ | OC$_6$H$_5$ | 1 | N | | |
| 134 | 4-Cl—C$_6$H$_4$ | CH$_3$ | SC$_6$H$_5$ | 1 | N | | |
| 135 | 4-Cl—C$_6$H$_4$ | CH$_3$ | O—C$_6$H$_4$—Cl (4-Cl-phenoxy) | 1 | N | | |
| 136 | 4-Cl—C$_6$H$_4$ | CH$_3$ | OCH$_3$ | 2 | N | | |
| 137 | 4-Cl—C$_6$H$_4$ | CH$_3$ | SCH$_3$ | 2 | N | | |
| 138 | 4-Cl—C$_6$H$_4$ | CH$_3$ | N(CH$_3$)$_2$ | 2 | N | | |
| 139 | 4-Cl—C$_6$H$_4$ | CH$_3$ | OCH$_3$ | 3 | N | | |
| 140 | 4-Cl—C$_6$H$_4$ | CH$_3$ | SCH$_3$ | 3 | N | | |
| 141 | 4-Cl—C$_6$H$_4$ | CH$_3$ | OCH$_3$ | 5 | N | | |
| 142 | 4-Cl—C$_6$H$_4$ | C$_6$H$_5$ | OCH$_3$ | 1 | N | | |
| 143 | 4-Cl—C$_6$H$_4$ | 4-F—C$_6$H$_4$ | OCH$_3$ | 1 | N | | |
| 144 | 4-Cl—C$_6$H$_4$ | 2-Cl—C$_6$H$_4$ | OCH$_3$ | 1 | N | | |
| 145 | 4-Br—C$_6$H$_4$ | iso-C$_3$H$_7$ | OCH$_3$ | 1 | N | | |
| 146 | 4-Br—C$_6$H$_4$ | cyclohexyl | OCH$_3$ | 1 | N | | |
| 147 | 4-Br—C$_6$H$_4$ | CH$_3$ | OCH$_3$ | 0 | N | | |
| 148 | 4-Br—C$_6$H$_4$ | CH$_3$ | OC$_2$H$_5$ | 0 | N | | |
| 149 | 4-Br—C$_6$H$_4$ | CH$_3$ | SCH$_3$ | 0 | N | | |
| 150 | 4-Br—C$_6$H$_4$ | CH$_3$ | O—C$_6$H$_4$—Cl (4-Cl-phenoxy) | 0 | N | | |
| 151 | 4-Br—C$_6$H$_4$ | CH$_3$ | OCH$_3$ | 1 | N | | |
| 152 | 4-Br—C$_6$H$_4$ | CH$_3$ | OC$_2$H$_5$ | 1 | N | | |
| 153 | 4-Br—C$_6$H$_4$ | CH$_3$ | SC$_6$H$_5$ | 1 | N | | |
| 154 | 4-Br—C$_6$H$_4$ | CH$_3$ | O—C$_6$H$_4$—Cl (4-Cl-phenoxy) | 1 | N | | |
| 155 | 4-Br—C$_6$H$_4$ | CH$_3$ | OCH$_3$ | 2 | N | | |
| 156 | 4-Br—C$_6$H$_4$ | CH$_3$ | SCH$_3$ | 2 | N | | |
| 157 | 4-Br—C$_6$H$_4$ | CH$_3$ | NH—C$_6$H$_5$ | 2 | N | | |
| 158 | 4-Br—C$_6$H$_4$ | CH$_3$ | OCH$_3$ | 3 | N | | |
| 159 | 4-Br—C$_6$H$_4$ | CH$_3$ | SCH$_3$ | 3 | N | | |
| 160 | 4-Br—C$_6$H$_4$ | CH$_3$ | OCH$_3$ | 4 | N | | |
| 161 | 4-Br—C$_6$H$_4$ | CH$_3$ | OCH$_3$ | 4 | CH | | |
| 162 | 4-Br—C$_6$H$_4$ | CH$_3$ | OCH$_3$ | 5 | N | | |
| 163 | 4-Br—C$_6$H$_4$ | CH$_3$ | OCH$_3$ | 5 | CH | | |
| 164 | 2-F—C$_6$H$_4$ | CH$_3$ | OCH$_3$ | 0 | N | | |
| 165 | 2-F—C$_6$H$_4$ | CH$_3$ | OCH$_3$ | 0 | CH | | |
| 166 | 2-F—C$_6$H$_4$ | CH$_3$ | OC$_2$H$_5$ | 0 | N | | |
| 167 | 2-F—C$_6$H$_4$ | CH$_3$ | OCH$_3$ | 1 | N | | |
| 168 | 2-F—C$_6$H$_4$ | CH$_3$ | SCH$_3$ | 1 | N | | |
| 169 | 2-F—C$_6$H$_4$ | CH$_3$ | OCH$_3$ | 2 | N | | |
| 170 | 2-F—C$_6$H$_4$ | CH$_3$ | OCH$_3$ | 3 | N | | |
| 171 | 2-F—C$_6$H$_4$ | CH$_3$ | OCH$_3$ | 4 | N | | |
| 172 | 2-Cl—C$_6$H$_4$ | CH$_3$ | OCH$_3$ | 0 | N | | |
| 173 | 2-Cl—C$_6$H$_4$ | CH$_3$ | OCH$_3$ | 1 | N | | |
| 174 | 2-Cl—C$_6$H$_4$ | CH$_3$ | OCH$_3$ | 1 | CH | | |
| 175 | 2-Cl—C$_6$H$_4$ | CH$_3$ | OCH$_3$ | 2 | N | | |
| 176 | 2-Cl—C$_6$H$_4$ | CH$_3$ | OCH$_3$ | 3 | N | | |
| 177 | 2-Cl—C$_6$H$_4$ | CH$_3$ | OCH$_3$ | 4 | N | | |

TABLE-continued

Fungicidal azolylethane derivatives

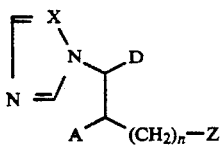

I

| Ex. | A | Z | D | n | X | m.p./IR (cm$^{-1}$) | Isomer* |
|---|---|---|---|---|---|---|---|
| 178 | 2-Cl—C$_6$H$_4$ | CH$_3$ | OCH$_3$ | 5 | N | | |
| 179 | 4-OCH$_3$—C$_6$H$_4$ | CH$_3$ | OCH$_3$ | 0 | N | | |
| 180 | 4-OCH$_3$—C$_6$H$_4$ | CH$_3$ | OCH$_3$ | 1 | N | | |
| 181 | 4-OCH$_3$—C$_6$H$_4$ | CH$_3$ | SCH$_3$ | 1 | N | | |
| 182 | 4-OCH$_3$—C$_6$H$_4$ | CH$_3$ | O—C$_6$H$_4$—Cl (4-) | 1 | N | | |
| 183 | 4-OCH$_3$—C$_6$H$_4$ | CH$_3$ | OCH$_3$ | 2 | N | | |
| 184 | 4-OCH$_3$—C$_6$H$_4$ | CH$_3$ | OCH$_3$ | 3 | N | | |
| 185 | 4-CH$_3$—C$_6$H$_4$ | CH$_3$ | OCH$_3$ | 0 | N | | |
| 186 | 4-CH$_3$—C$_6$H$_4$ | CH$_3$ | OCH$_3$ | 1 | N | | |
| 187 | 4-CH$_3$—C$_6$H$_4$ | CH$_3$ | SCH$_3$ | 1 | N | | |
| 188 | 4-CH$_3$—C$_6$H$_4$ | CH$_3$ | O—C$_6$H$_4$—Cl (4-) | 1 | N | | |
| 189 | 4-CH$_3$—C$_6$H$_4$ | CH$_3$ | OCH$_3$ | 3 | N | | |
| 190 | 4-tert-butyl-C$_6$H$_4$ | CH$_3$ | OCH$_3$ | 1 | N | | |
| 191 | 4-tert-butyl-C$_6$H$_4$ | CH$_3$ | OCH$_3$ | 2 | N | | |
| 192 | 1-naphthyl | CH$_3$ | OCH$_3$ | 0 | N | | |
| 193 | 1-naphthyl | CH$_3$ | OCH$_3$ | 1 | N | | |
| 194 | 1-naphthyl | CH$_3$ | OCH$_3$ | 2 | N | | |
| 195 | 1-naphthyl | CH$_3$ | SCH$_3$ | 2 | N | | |
| 196 | 1-naphthyl | CH$_3$ | O—C$_6$H$_4$—Cl (4-) | 0 | N | | |
| 197 | 2-naphthyl | CH$_3$ | OCH$_3$ | 0 | N | | |
| 198 | 2-naphthyl | CH$_3$ | OCH$_3$ | 1 | N | | |
| 199 | 2-naphthyl | CH$_3$ | SCH$_3$ | 1 | N | | |
| 200 | 1-naphthyl | CH$_3$ | O—C$_6$H$_4$—Cl (4-) | 1 | N | | |
| 201 | 2-naphthyl | CH$_3$ | OCH$_3$ | 2 | N | | |
| 202 | 2-naphthyl | CH$_3$ | OCH$_3$ | 3 | N | | |
| 203 | 2-naphthyl | CH$_3$ | OCH$_3$ | 4 | N | | |
| 204 | 2-naphthyl | CH$_3$ | OCH$_3$ | 5 | N | | |
| 205 | tert.—C$_4$H$_9$ | 4-F—C$_6$H$_4$ | OCH$_3$ | 0 | N | | |
| 206 | tert.—C$_4$H$_9$ | 4-F—C$_6$H$_4$ | OC$_2$H$_5$ | 0 | N | | |
| 207 | tert.—C$_4$H$_9$ | 4-F—C$_6$H$_4$ | SCH$_3$ | 0 | N | | |
| 208 | tert.—C$_4$H$_9$ | 4-F—C$_6$H$_4$ | O—C$_6$H$_4$—Cl (4-) | 0 | N | | |

TABLE-continued

Fungicidal azolylethane derivatives

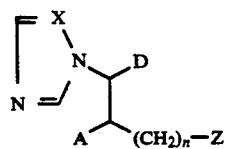

I

| Ex. | A | Z | D | n | X | m.p./IR (cm$^{-1}$) | Isomer* |
|---|---|---|---|---|---|---|---|
| 209 | tert.—$C_4H_9$ | 4-Cl—$C_6H_4$ | $OCH_3$ | 0 | N | | |
| 210 | tert.—$C_4H_9$ | 4-Cl—$C_6H_4$ | $OC_2H_5$ | 1 | N | | |
| 211 | tert.—$C_4H_9$ | 4-Cl—$C_6H_4$ | $SCH_3$ | 0 | N | | |
| 212 | tert.—$C_4H_9$ | 2-Cl—$C_6H_4$ | $OCH_3$ | 0 | N | | |
| 213 | tert.—$C_4H_9$ | 2-Cl—$C_6H_4$ | $OC_2H_4$ | 0 | N | | |
| 214 | tert.—$C_4H_9$ | 2-Cl—$C_6H_4$ | O—$C_6H_4$—Cl (4) | 0 | N | | |
| 215 | tert.—$C_4H_9$ | 2,4-$Cl_2$—$C_6H_3$ | $OCH_3$ | 0 | N | | |
| 216 | tert.—$C_4H_9$ | 2,4-$Cl_2$—$C_6H_3$ | $OCH_3$ | 1 | N | | |
| 217 | tert.—$C_4H_9$ | 2,4-$Cl_2$—$C_6H_3$ | $OCH_3$ | 2 | N | | |
| 218 | tert.—$C_4H_9$ | 2,4-$Cl_2$—$C_6H_3$ | $OC_2H_5$ | 1 | N | | |
| 219 | tert.—$C_4H_9$ | 4-$OCH_3$—$C_6H_4$ | $OCH_3$ | 0 | N | | |
| 220 | tert.—$C_4H_9$ | 4-$CH_3$—$C_6H_4$ | $OCH_3$ | 1 | N | | |
| 221 | tert.—$C_4H_9$ | 4-$NO_2$—$C_6H_4$ | $OCH_3$ | 1 | N | | |
| 222 | tert.—$C_4H_9$ | cyclohexyl | $OCH_3$ | 0 | N | | |
| 223 | tert.—$C_4H_9$ | cyclohexyl | $OC_2H_5$ | 0 | N | | |
| 224 | tert.—$C_4H_9$ | cyclohexyl | $OCH_3$ | 1 | N | | |
| 225 | 2,4-Cl—$C_6H_3$ | $CH_3$ | S—$C_6H_5$ | 2 | N | 2959, 1474, 1273, 1136, 822 | $D_1:D_2 = 2:1$ |
| 226 | $C_6H_5$ | $CH_3$ | S—$C_6H_5$ | 1 | N | 2965, 1499, 1274, 1136, 744, 700 | $D_1:D_2 = 2:1$ |
| 227 | $C_6H_5$ | $CH_3$ | S—$C_6H_4$—Cl (4) | 1 | N | 2969, 1498, 1476, 1274, 1136, 1094 1013, 823, 700 | $D_1:D_2 = 2:1$ |
| 228 | 2,4-$Cl_2$—$C_6H_3$ | $CH_3$ | S—$C_6H_5$ | 4 | N | 2955, 2929, 1501, 1474, 1273, 1136, 742, 691 | $D_1:D_2 = 1:1$ |
| 229 | $C_6H_5$ | 2-F—$C_6H_4$ | S—$C_6H_5$ | 0 | N | 1491, 1480, 1453, 1275, 757, 739, 697 | $D_1:D_2 = 1:1$ |
| 230 | $C_6H_5$ | $CH_3$ | S—$C_6H_4$—Cl (4) | 3 | N | 2955, 2930, 1476, 1095, 1013, 812, 700 | $D_1:D_2 = 1:1$ |
| 231 | $C_6H_5$ | $CH_3$ | S—$C_6H_4$—F (4) | 3 | N | 2956, 1490, 1229, 820, 700 | $D_1:D_2 = 1:1$ |
| 232 | 4-Cl—$C_6H_4$ | $CH_3$ | S—$C_6H_5$ | 0 | N | 1598, 1476, 1273, 1137, 742, 690 | $D_1:D_2 = 2:1$ |
| 233 | 4-Cl—$C_6H_4$ | $CH_3$ | S—$C_6H_5$ | 0 | N | 108–110° C. | enantiomer mixture |
| 234 | $C_6H_5$ | $C_6H_5$ | $OCH_3$ | 0 | N | | |
| 235 | $C_6H_5$ | $C_6H_5$ | $OCH_3$ | 0 | CH | | |
| 236 | $C_6H_5$ | $C_6H_5$ | $OC_2H_5$ | 0 | N | | |
| 237 | $C_6H_5$ | 2-Cl—$C_6H_4$ | $OCH_3$ | 0 | N | | |
| 238 | $C_6H_5$ | 4-CL—$C_6H_4$ | $OCH_3$ | 0 | N | | |
| 239 | $C_6H_5$ | 2,4-$Cl_2$—$C_6H_3$ | $OCH_3$ | 0 | N | | |
| 240 | $C_6H_5$ | 2-F—$C_6H_4$ | $OCH_3$ | 0 | N | | |
| 241 | $C_6H_5$ | 4-F—$C_6H_4$ | $OCH_3$ | 0 | N | | |
| 242 | $C_6H_5$ | 4-F—$C_6H_4$ | $OC_2H_5$ | 0 | N | | |
| 243 | $C_6H_5$ | 2-$CH_3$—$C_6H_4$ | $OCH_3$ | 0 | N | | |
| 244 | $C_6H_5$ | 2,4-$(CH_3)_2$—$C_6H_3$ | $OCH_3$ | 0 | N | | |
| 245 | $C_6H_5$ | 4-$CF_3$—$C_6H_4$ | $OCH_3$ | 0 | N | | |
| 246 | $C_6H_5$ | 4-Br—$C_6H_4$ | $OCH_3$ | 0 | N | | |
| 247 | $C_6H_5$ | 4-$OCH_3$—$C_6H_4$ | $OCH_3$ | 0 | N | | |
| 248 | $C_6H_5$ | 4-$CH_3$—$C_6H_4$ | $OCH_3$ | 0 | N | | |
| 249 | $C_6H_5$ | 2-naphtyl | $OCH_3$ | 0 | N | | |

TABLE-continued

Fungicidal azolylethane derivatives

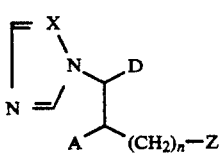

I

| Ex. | A | Z | D | n | X | m.p./IR (cm$^{-1}$) | Isomer* |
|---|---|---|---|---|---|---|---|
| 250 | 4-F—C$_6$H$_4$ | 2-F—C$_6$H$_4$ | OCH$_3$ | 0 | N | | |
| 251 | 4-F—C$_6$H$_4$ | 2-F—C$_6$H$_4$ | OCH$_3$ | 0 | CH | | |
| 252 | 4-F—C$_6$H$_4$ | 2-F—C$_6$H$_4$ | OC$_2$H$_5$ | 0 | N | | |
| 253 | 4-F—C$_6$H$_4$ | 2-F—C$_6$H$_4$ | OCH(CH$_3$)$_2$ | 0 | N | | |
| 254 | 4-F—C$_6$H$_4$ | 4-F—C$_6$H$_4$ | OCH$_3$ | 0 | N | | |
| 255 | 4-F—C$_6$H$_4$ | 4-F—C$_6$H$_4$ | OCH$_3$ | 0 | CH | | |
| 256 | 4-F—C$_6$H$_4$ | 4-F—C$_6$H$_4$ | OC$_2$H$_5$ | 0 | N | | |
| 257 | 4-F—C$_6$H$_4$ | 4-F—C$_6$H$_4$ | OC$_2$H$_5$ | 0 | CH | | |
| 258 | 4-F—C$_6$H$_4$ | 4-F—C$_6$H$_4$ | OCH(CH$_3$)$_2$ | 0 | N | | |
| 259 | 4-F—C$_6$H$_4$ | 4-F—C$_6$H$_4$ | OCH$_2$C$_6$H$_5$ | 0 | N | | |
| 260 | 4-F—C$_6$H$_4$ | 2-Cl—C$_6$H$_4$ | OCH$_3$ | 0 | N | | |
| 261 | 4-F—C$_6$H$_4$ | 2-Cl—C$_6$H$_4$ | OCH$_3$ | 0 | CH | | |
| 262 | 4-F—C$_6$H$_4$ | 2-Cl—C$_6$H$_4$ | OC$_2$H$_5$ | 0 | N | | |
| 263 | 4-F—C$_6$H$_4$ | 2-Cl—C$_6$H$_4$ | OC$_2$H$_5$ | 0 | CH | | |
| 264 | 4-F—C$_6$H$_4$ | 2-Cl—C$_6$H$_4$ | OCH(CH$_3$)$_2$ | 0 | N | | |
| 265 | 4-F—C$_6$H$_4$ | 2-Cl—C$_6$H$_4$ | OCH(CH$_3$)$_2$ | 0 | CH | | |
| 266 | 4-F—C$_6$H$_4$ | 4-Cl—C$_6$H$_4$ | OCH$_3$ | 0 | N | | |
| 267 | 4-F—C$_6$H$_4$ | 4-Cl—C$_6$H$_4$ | OCH$_3$ | 0 | CH | | |
| 268 | 4-F—C$_6$H$_4$ | 4-Cl—C$_6$H$_4$ | OC$_2$H$_5$ | 0 | N | | |
| 269 | 4-F—C$_6$H$_4$ | 4-Cl—C$_6$H$_4$ | OC$_2$H$_5$ | 0 | CH | | |
| 270 | 4-F—C$_6$H$_4$ | 4-Cl—C$_6$H$_4$ | OCH(CH$_3$)$_2$ | 0 | N | | |
| 271 | 4-F—C$_6$H$_4$ | 2,4-Cl$_2$—C$_6$H$_3$ | OCH$_3$ | 0 | N | | |
| 272 | 4-F—C$_6$H$_4$ | 2,4-Cl$_2$—C$_6$H$_3$ | OCH$_3$ | 0 | CH | | |
| 273 | 4-F—C$_6$H$_4$ | 2,4-Cl$_2$—C$_6$H$_3$ | OC$_2$H$_5$ | 0 | N | | |
| 274 | 4-F—C$_6$H$_4$ | 2,4-Cl$_2$—C$_6$H$_3$ | OC$_2$H$_5$ | 0 | N | | |
| 275 | 4-F—C$_6$H$_4$ | 2,4-Cl$_2$—C$_6$H$_3$ | OCH(CH$_3$)$_2$ | 0 | N | | |
| 276 | 4-F—C$_6$H$_4$ | 4-Br—C$_6$H$_4$ | OCH$_3$ | 0 | N | | |
| 277 | 4-F—C$_6$H$_4$ | 4-Br—C$_6$H$_4$ | OC$_2$H$_5$ | 0 | N | | |
| 278 | 4-F—C$_6$H$_4$ | 2-CH$_3$—C$_6$H$_4$ | OCH$_3$ | 0 | N | | |
| 279 | 4-F—C$_6$H$_4$ | 2-CH$_3$—C$_6$H$_4$ | OCH$_3$ | 0 | CH | | |
| 280 | 4-F—C$_6$H$_4$ | 2-CH$_3$—C$_6$H$_4$ | OC$_2$H$_5$ | 0 | N | | |
| 281 | 4-F—C$_6$H$_4$ | 2-CH$_3$—C$_6$H$_4$ | OCH(CH$_3$)$_2$ | 0 | N | | |
| 282 | 4-F—C$_6$H$_4$ | 4-CH$_3$—C$_6$H$_4$ | OCH$_3$ | 0 | N | | |
| 283 | 4-F—C$_6$H$_4$ | 4-CH$_3$—C$_6$H$_4$ | OCH$_3$ | 0 | CH | | |
| 284 | 4-F—C$_6$H$_4$ | 4-CH$_3$—C$_6$H$_4$ | OC$_2$H$_5$ | 0 | N | | |
| 285 | 4-F—C$_6$H$_4$ | 4-CH$_3$—C$_6$H$_4$ | OCH(CH$_3$)$_2$ | 0 | N | | |
| 286 | 4-F—C$_6$H$_4$ | 2,4-(CH$_3$)$_2$—C$_6$H$_3$ | OCH$_3$ | 0 | N | | |
| 287 | 4-F—C$_6$H$_4$ | 2,4-(CH$_3$)$_2$—C$_6$H$_3$ | OC$_2$H$_5$ | 0 | N | | |
| 288 | 4-F—C$_6$H$_4$ | 4-CF$_3$—C$_6$H$_4$ | OCH$_3$ | 0 | N | | |
| 289 | 4-F—C$_6$H$_4$ | 4-CF$_3$—C$_6$H$_4$ | OC$_2$H$_5$ | 0 | N | | |
| 290 | 4-F—C$_6$H$_4$ | 4-OCH$_3$—C$_6$H$_4$ | OCH$_3$ | 0 | N | | |
| 291 | 4-F—C$_6$H$_4$ | 4-OCH$_3$—C$_6$H$_4$ | OC$_2$H$_5$ | 0 | N | | |
| 292 | 4-Cl—C$_6$H$_4$ | 2-F—C$_6$H$_4$ | OCH$_3$ | 0 | N | | |
| 293 | 4-Cl—C$_6$H$_4$ | 2-F—C$_6$H$_4$ | OC$_2$H$_5$ | 0 | N | | |
| 294 | 4-Cl—C$_6$H$_4$ | 2-Cl—C$_6$H$_4$ | OCH$_3$ | 0 | N | | |
| 295 | 4-Cl—C$_6$H$_4$ | 2-Cl—C$_6$H$_4$ | OC$_2$H$_5$ | 0 | N | | |
| 296 | 4-Cl—C$_6$H$_4$ | 4-Cl—C$_6$H$_4$ | OCH$_3$ | 0 | N | | |
| 297 | 4-Cl—C$_6$H$_4$ | 4-Cl—C$_6$H$_4$ | OCH$_3$ | 0 | CH | | |
| 298 | 4-Cl—C$_6$H$_4$ | 4-Cl—C$_6$H$_4$ | OC$_2$H$_5$ | 0 | N | | |
| 299 | 4-Cl—C$_6$H$_4$ | 4-Cl—C$_6$H$_4$ | OC$_2$H$_5$ | 0 | CH | | |
| 300 | 4-Cl—C$_6$H$_4$ | 4-Cl—C$_6$H$_4$ | OCH(CH$_3$)$_2$ | 0 | N | | |
| 301 | 4-Cl—C$_6$H$_4$ | 4-Cl—C$_6$H$_4$ | OCH(CH$_3$)$_2$ | 0 | CH | | |
| 302 | 4-Cl—C$_6$H$_4$ | 2,4-Cl—C$_6$H$_3$ | OCH$_3$ | 0 | N | | |
| 303 | 4-Cl—C$_6$H$_4$ | 2,4-Cl—C$_6$H$_3$ | OC$_2$H$_5$ | 0 | N | | |
| 304 | 4-Cl—C$_6$H$_4$ | 2-CH$_3$—C$_6$H$_4$ | OCH$_3$ | 0 | N | | |
| 305 | 4-Cl—C$_6$H$_4$ | 2-CH$_3$—C$_6$H$_4$ | OC$_2$H$_5$ | 0 | N | | |
| 306 | 4-Cl—C$_6$H$_4$ | 2,4-(CH$_3$)$_2$—C$_6$H$_3$ | OCH$_3$ | 0 | N | | |
| 307 | 4-Cl—C$_6$H$_4$ | 2,4-(CH$_3$)$_2$—C$_6$H$_3$ | OC$_2$H$_5$ | 0 | N | | |
| 308 | 4-Cl—C$_6$H$_4$ | 4-CF$_3$—C$_6$H$_4$ | OCH$_3$ | 0 | N | | |
| 309 | 4-Cl—C$_6$H$_4$ | 4-CF$_3$—C$_6$H$_4$ | OC$_2$H$_5$ | 0 | N | | |
| 310 | 4-Cl—C$_6$H$_4$ | 4-Br—C$_6$H$_4$ | OCH$_3$ | 0 | N | | |
| 311 | 4-Cl—C$_6$H$_4$ | 4-Br—C$_6$H$_4$ | OC$_2$H$_5$ | 0 | N | | |
| 312 | 4-Cl—C$_6$H$_4$ | 4-CH$_3$—C$_6$H$_4$ | OCH$_3$ | 0 | N | | |
| 313 | 4-Cl—C$_6$H$_4$ | 4-CH$_3$—C$_6$H$_4$ | OCH$_3$ | 0 | CH | | |
| 314 | 4-Cl—C$_6$H$_4$ | 4-CH$_3$—C$_6$H$_4$ | OC$_2$H$_5$ | 0 | N | | |
| 315 | 4-CH$_3$—C$_6$H$_4$ | 2-F—C$_6$H$_4$ | OCH$_3$ | 0 | N | | |
| 316 | 4-CH$_3$—C$_6$H$_4$ | 2-Cl—C$_6$H$_4$ | OCH$_3$ | 0 | N | | |
| 317 | 4-CH$_3$—C$_6$H$_4$ | 2,4-Cl$_2$—C$_6$H$_3$ | OCH$_3$ | 0 | N | | |
| 318 | 4-CH$_3$—C$_6$H$_4$ | 4-Br—C$_6$H$_4$ | OCH$_3$ | 0 | N | | |
| 319 | 4-CH$_3$—C$_6$H$_4$ | 4-CF$_3$—C$_6$H$_4$ | OCH$_3$ | 0 | N | | |

TABLE-continued

Fungicidal azolylethane derivatives

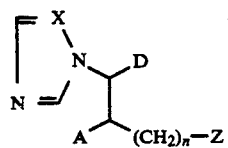

I

| Ex. | A | Z | D | n | X | m.p./IR (cm$^{-1}$) | Isomer* |
|---|---|---|---|---|---|---|---|
| 320 | 4-CH$_3$—C$_6$H$_4$ | 2-CH$_3$—C$_6$H$_4$ | OCH$_3$ | 0 | N | | |
| 321 | 4-CH$_3$—C$_6$H$_4$ | 4-CH$_3$—C$_6$H$_4$ | OCH$_3$ | 0 | N | | |
| 322 | 4-CH$_3$—C$_6$H$_4$ | 4-CH$_3$—C$_6$H$_4$ | OCH$_3$ | 0 | CH | | |
| 323 | 4-CH$_3$—C$_6$H$_4$ | 4-CH$_3$—C$_6$H$_4$ | OC$_2$H$_5$ | 0 | N | | |
| 324 | 4-CH$_3$—C$_6$H$_4$ | 4-CH$_3$—C$_6$H$_4$ | OC$_2$H$_5$ | 0 | CH | | |
| 325 | 4-CH$_3$—C$_6$H$_4$ | 4-CH$_3$—C$_6$H$_4$ | OCH(CH$_3$)$_2$ | 0 | N | | |
| 326 | 4-CH$_3$—C$_6$H$_4$ | 4-OCH$_3$—C$_6$H$_4$ | OCH$_3$ | 0 | N | | |
| 327 | 4-CH$_3$—C$_6$H$_4$ | 4-OCH$_3$—C$_6$H$_4$ | OC$_2$H$_5$ | 0 | N | | |
| 328 | 4-OCH$_3$—C$_6$H$_4$ | 2-F—C$_6$H$_4$ | OCH$_3$ | 0 | N | | |
| 329 | 4-OCH$_3$—C$_6$H$_4$ | 2-Cl—C$_6$H$_4$ | OCH$_3$ | 0 | N | | |
| 330 | 4-OCH$_3$—C$_6$H$_4$ | 2,4-Cl$_2$—C$_6$H$_3$ | OCH$_3$ | 0 | N | | |
| 331 | 4-OCH$_3$—C$_6$H$_4$ | 4-Br—C$_6$H$_4$ | OCH$_3$ | 0 | N | | |
| 332 | 4-OCH$_3$—C$_6$H$_4$ | 4-CF—C$_6$H$_4$ | OCH$_3$ | 0 | N | | |
| 333 | 4-OCH$_3$—C$_6$H$_4$ | 2-CH$_3$—C$_6$H$_4$ | OCH$_3$ | 0 | N | | |
| 334 | 4-OCH$_3$—C$_6$H$_4$ | 2,4-(CH$_3$)$_2$—C$_6$H$_3$ | OCH$_3$ | 0 | N | | |
| 335 | 4-OCH$_3$—C$_6$H$_4$ | 4-OCH$_3$—C$_6$H$_4$ | OCH$_3$ | 0 | N | | |
| 336 | 4-OCH$_3$—C$_6$H$_4$ | 4-OCH$_3$—C$_6$H$_4$ | OCH$_3$ | 0 | CH | | |
| 337 | 4-OCH$_3$—C$_6$H$_4$ | 4-OCH$_3$—C$_6$H$_4$ | OC$_2$H$_5$ | 0 | N | | |
| 338 | 4-OCH$_3$—C$_6$H$_4$ | 4-OCH$_3$—C$_6$H$_4$ | OC$_2$H$_5$ | 0 | CH | | |
| 339 | 4-OCH$_3$—C$_6$H$_4$ | 4-OCH$_3$—C$_6$H$_4$ | OCH(CH$_3$)$_2$ | 0 | N | | |
| 340 | 4-CF$_3$—C$_6$H$_4$ | 2-F—C$_6$H$_4$ | OCH$_3$ | 0 | N | | |
| 341 | 4-CF$_3$—C$_6$H$_4$ | 2-Cl—C$_6$H$_4$ | OCH$_3$ | 0 | N | | |
| 342 | 4-CF$_3$—C$_6$H$_4$ | 2-CH$_3$—C$_6$H$_4$ | OCH$_3$ | 0 | N | | |
| 343 | 4-CF$_3$—C$_6$H$_4$ | 2,4-(CH$_3$)$_2$—C$_6$H$_4$ | OCH$_3$ | 0 | N | | |
| 344 | 4-CF$_3$—C$_6$H$_4$ | 4-Br—C$_6$H$_4$ | OCH$_3$ | 0 | N | | |
| 345 | 4-CF$_3$—C$_6$H$_4$ | 4-CF$_3$—C$_6$H$_4$ | OCH$_3$ | 0 | N | | |
| 346 | 4-CF$_3$—C$_6$H$_4$ | 4-CF$_3$—C$_6$H$_4$ | OCH$_3$ | 0 | CH | | |
| 347 | 4-CF$_3$—C$_6$H$_4$ | 4-CF$_3$—C$_6$H$_4$ | OC$_2$H$_5$ | 0 | N | | |
| 348 | 4-CF$_3$—C$_6$H$_4$ | 4-CF$_3$—C$_6$H$_4$ | OC$_2$H$_5$ | 0 | CH | | |
| 349 | 4-CF$_3$—C$_6$H$_4$ | 4-CF$_3$—C$_6$H$_4$ | OCH(CH$_3$)$_2$ | 0 | N | | |

*Ratio of the diastereomers formed

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea gray mold in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticullium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel compounds may exercise a variety of influences on practically all plant development stages, and are therefore used as growth regulators. The diversity of action of growth regulators depends especially on
a) the type and variety of plant;
b) the time applied, with reference to the development stage of the plants and the time of the year;
c) the place and method of application seed treatment, soil treatment, or application to foliage;
d) climatic factors. e.g., average temperature, amount of precipitate, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.
A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots suckers in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening abscission of the adherence of stalks to the branches of citrus fruit, olive trees and other kinds of pomes, drupes and indehiscent fruit. The same mechanism. i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized because, inter alia, the size of the stomata opening is reduced;

a thicker epidermis and cuticle are formed;

penetration of the soil by the roots is improved;

the micro-climate in the stand is favorably influenced by the more compact growth.

The active ingredients according to the invention may be applied not only to the seed (as a disinfectant), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50. and preferably from 0.01 to 10, g per kg of seed are generally required.

For foliage and soil treatment, amounts of from 0.01 to 10, and preferably from 0.02 to 3, kg/ha are generally considered to be sufficient.

The novel substances may be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants if water is used as solvent it is also possible to employ other organic solvents as auxiliary solvents, suitable auxiliaries for this purpose are solvents such as aromatics (e.g., xylene, chlorinated aromatics (e.g., chlorobenzenes), paraffins (e.g.. crude oil fractions), alcohols (e.g., methanol, butanol), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers and other surfactants, such as nonionic and anionic emulsifiers (e.g., polyoxyethylene fatty alcohol ethers, alkyl sulfonates); and dispersants such as lignin, sulfite waste liquors and methylcellulose.

The fungicidal agents generally contain from 0.1 to 95 and preferably from 0.5 to 90, wt. % of active ingredient. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 Parts by weight of compound no. 27 dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 42 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein an aqueous dispersion is obtained.

IV. 20 parts by weight of compound no. 44 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein an aqueous dispersion is obtained.

V. 80 parts by weight of compound no. 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a Spray liquor is obtained.

VI. 3 parts by weight of compound no. 27 is intimately mixed with 97 parts by weight of particulate kaolin. A dust is obtained containing 3% by weight of the active ingredient.

VII. 30 parts by weight of compound no. 42 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 44 is intimately mixed with 10 parts by weight of the sodium salt of a phenolsulfonic acid-urea-formaldehyde condensate, 2 Parts of silica gel and 48 parts of water to give a stable aqueous dispersion. Dilution in water gives an aqueous dispersion.

IX. 20 parts by weight of compound no. 1 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLES

For comparison purposes, the compounds 1-(1,2,4-triazol-1-yl)-1-phenylthio-2-methyl-2-phenylpropane (A) and 1-(1,2,4-triazol-1-yl)-1-(4-chlorophenylthio)-2-methyl-2-phenylpropane (B) disclosed n EP 91,219 were used.

USE EXAMPLE 1

Action on *Pyricularia oryzae* (protective)

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of *Pyricularia oryzae*. The plants were then set up in climatic cabinets at from 22° to 24° C. and a relative humidity of 95 to 99%. The extent of fungus spread was assessed after 6 days.

The results show that active ingredients 1, 27, 42, 44, 228 and 232, applied as 0.05 wt. % spray liquors, have a better fungicidal action (90%) than prior art active ingredients A and B (30%).

USE EXAMPLE 2

Action on *Pyrenophora teres*

Barley seedlings of the "Igri" variety were Sprayed to runoff at the two-leaf stage with aqueous suspensions consisting dry basis of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredients 1, 27, 49, 134, 226 and 228, applied as 0.05% spray liquors, have a better fungicidal action (90%) than prior art active ingredients A and B (10%).

We claim:

1. A compound of the formula

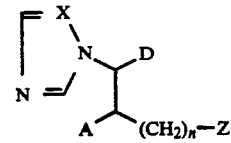

wherein A is 2,4-dichlorophenyl, Z is methyl, D is methoxy or ethoxy, n is 0, 1, 2 or 3, and X is N.

2. The compound of claim 1, wherein D is methoxy and n is 2.

3. The compound of claim 1, wherein D is methoxy and n is 3.

4. The compound of claim 1, wherein D is ethoxy and n is 3.

5. A fungicide composition, comprising a carrier and an effective amount of a compound of the formula

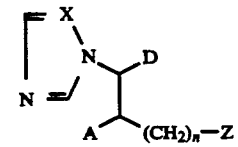

wherein A is 2,4-dichlorophenyl, Z is methyl, D is methoxy or ethoxy, n is 0, 1, 2 or 3, and X is N.

6. The composition of claim 5, wherein D is methoxy and n is 2.

7. The composition of claim 5, wherein D is methoxy and n is 3.

8. The composition of claim 5, wherein D is ethoxy and n is 3.

9. A process for combating fungi, wherein a fungicidally effective amount of a compound of the formula

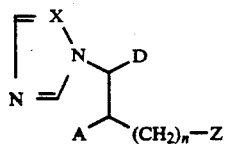

wherein A is 2,4-dichlorophenyl, Z is methyl, D is methoxy or ethoxy, n is 0, 1, 2 or 3, and X is N is allowed to act on said fungi or the soil, plants or seed threatened by fungus attack.

10. The process of claim 9, wherein D is methoxy and n is 2.

11. The process of claim 9, wherein D is methoxy and n is 3.

12. The process of claim 9, wherein D is ethoxy and n is 3.

13. A growth-regulating composition, comprising an effective amount of a compound of the formula

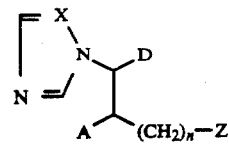

wherein A is 2,4-dichlorophenyl, Z is methyl, D is methoxy or ethoxy, n is 0, 1, 2 or 3, and X is N.

14. The process of claim 13, wherein D is methoxy and n is 2.

15. The process of claim 13, wherein D is methoxy and n is 3.

16. The process of claim 13, wherein D is ethoxy and n is 3.

* * * * *